US00PP17240P2

(12) United States Plant Patent
Ramirez

(10) Patent No.: US PP17,240 P2
(45) Date of Patent: Nov. 28, 2006

(54) ***PORTULACA* PLANT NAMED 'BALRIOROSE'**

(50) Latin Name: *Portulaca oleracea*
Varietal Denomination: Balriorose

(75) Inventor: Rolando Solano Ramirez, Dulce Nombre de Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 11 days.

(21) Appl. No.: 11/284,161

(22) Filed: Nov. 21, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Audrey Charles

(57) ABSTRACT

A new and distinct cultivar of *Portulaca* plant named 'Balriorose' characterized by its light rose-colored flowers, medium green-colored foliage, and vigorous, spreading growth habit.

1 Drawing Sheet

Latin name of genus and species of plant claimed: *Portulaca oleracea.*

Variety denomination: 'Balriorose'.

BACKGROUND OF THE INVENTION

The present invention relates to a new and distinct cultivar of *Portulaca* plant botanically known as *Portulaca oleracea* and hereinafter referred to by the cultivar name 'Balriorose'.

The new cultivar originated in a controlled breeding program in Cartago, Costa Rica during January 2002. The objective of the breeding program was the development of free flowering *Portulaca* cultivars with well-branched, and vigorous, spreading growth habit.

The female (seed) parent of the new cultivar was 'Wild Fire Rose', not patented, characterized by its pink-colored flowers, and vigorous, trailing growth habit. The male (pollen) parent of the new cultivar was 'Yubi Rose', not patented, characterized by its rose-colored flowers and trailing growth habit. The new cultivar was discovered and selected by the inventor as a single flowering plant within the progeny of the above stated cross-pollination during June 2002 in a controlled environment at Cartago, Costa Rica.

Asexual reproduction of the new cultivar by terminal stem cuttings since June 2002 at Cartago, Costa Rica and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balriorose' as a new and distinct cultivar of *Portulaca* plant:

1. Light rose-colored flowers;
2. Medium green-colored foliage; and
3. Vigorous, spreading growth habit.

Plants of the new cultivar differ from plants of the female parent primarily in flower color and flower size and from plants of the male parent primarily in flower color and growth habit.

Of the many commercially available *Portulaca* cultivars known to the inventor, the most similar in comparison to the new cultivar is 'Summer Joy Rose', U.S. Plant Pat. No. 12,285. However, in side by side comparisons, plants of the new cultivar differ from plants of 'Summer Joy Rose' in the following characteristics:

1. Plants of the new cultivar have more secondary branches than plants of 'Summer Joy Rose';
2. Plants of the new cultivar have a different flower color from plants of 'Summer Joy Rose'; and
3. Plants of the new cultivar have a different stigma color from plants of 'Summer Joy Rose'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balriorose'. The plants were grown in 10 cm pots for 11 weeks in a greenhouse at West Chicago, Ill.

DETAILED BOTANICAL DESCRIPTION

Figure 1:
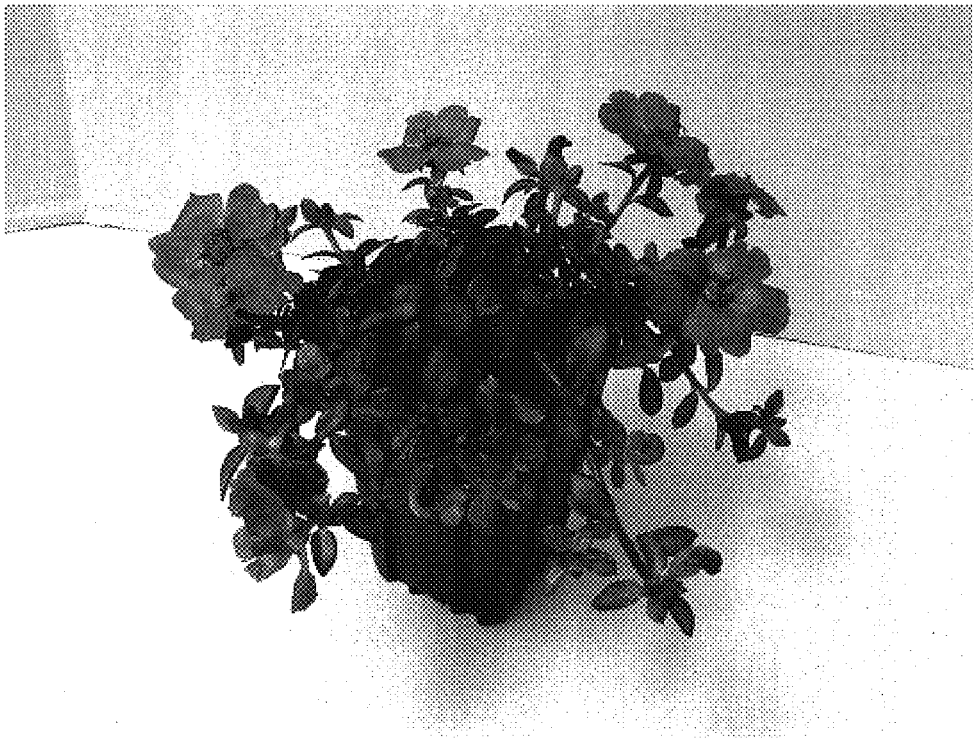
FIG. 1 illustrates a side view of the overall growth and flowering habit of 'Balriorose'.
Figure 2:
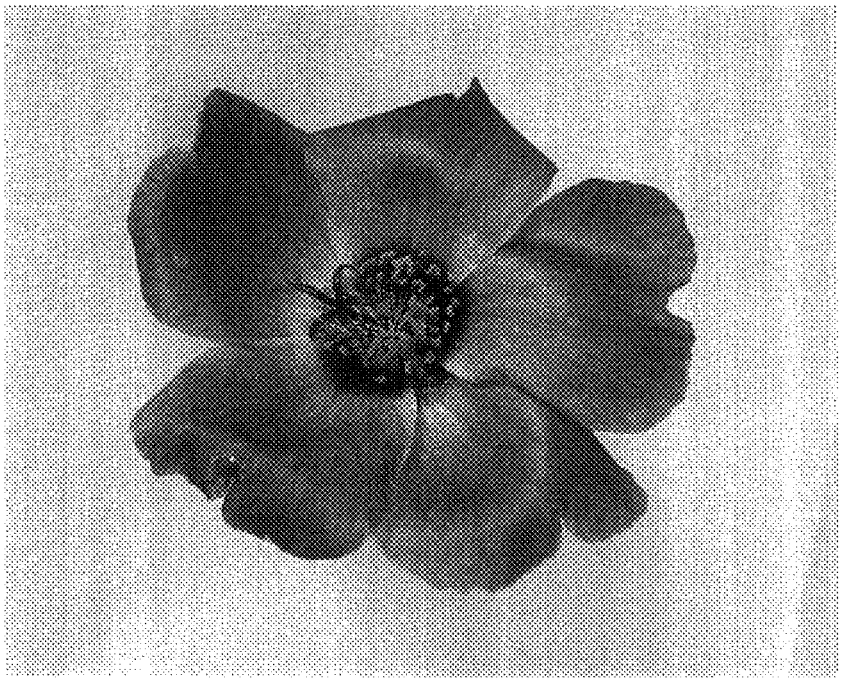
FIG. 2 illustrates a close-up view of an individual flower of 'Balriorose'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Aug. 8, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 11 weeks utilizing a soilless growth medium. Greenhouse temperatures were maintained at approximately 70° F. to 80° F. (21° C. to 26° C.) during the day and approximately 62° F. to 68° F. (17° C. to 20° C.) during the night. Greenhouse light levels of 5,000 to 10,000 footcandles were maintained during the day.

Botanical classification: *Portulaca oleracea* cultivar Balriorose.

Parentage:

*Female parent.*—'Wild Fire Rose', not patented.

*Male parent.*—'Yubi Rose', not patented.

Propagation:

*Type cutting.*—Terminal stem.

*Time to initiate roots.*—Approximately 4 to 7 days.

*Time to produce a rooted cutting.*—Approximately 14 to 21 days.

*Root description.*—Fibrous.

*Rooting habit.*—Freely branching.

Plant description:

*Crop time.*—Approximately 5 to 6 weeks from a rooted cutting.

*Growth habit and general appearance.*—Vigorous, spreading.

*Size.*—Height from soil level to top of plant plane: Approximately 8.2 cm. Height from soil level to top of foliage: Approximately 5.0 cm. Width: Approximately 32.9 cm.

*Branching habit.*—Freely basal branching. Approximately 5 main branches per plant and approximately 19 secondary branches per plant.

*Branch.*—Strength: Strong. Shape: Square in cross section with ridges along all four sides. Length: Approximately 15.3 cm. Diameter: Approximately 3.5 mm. Texture: Glabrous. Color of stem: 144B with overlay of 187A. Internode length at center of branch: Approximately 1.5 cm.

*Foliage.*—Number of leaves per main branch: Approximately 16. Fragrance: None. Form: Simple, fleshy succulent. Arrangement: Alternate. Aspect: Perpendicular or obtuse angle to stem. Shape: Obovate. Margin: Entire. Apex: Obtuse to slightly cuspidate. Base: Obtuse. Venation pattern: Pinnate. Length of mature leaf: Approximately 2.6 cm. Width of mature leaf: Approximately 1.6 cm. Depth of mature leaf: Approximately 2.0 mm. Texture of upper and lower surfaces: Glabrous. Color of upper surface of mature foliage: 137B with margin of 187B and venation of 150C. Color of lower surface of mature foliage: 137C with margin of 187B and venation of 150C. Petiole length: Approximately 2.0 mm. Petiole diameter: Approximately 2.0 mm. Petiole texture: Glabrous. Petiole color: 150C.

Flowering description:

*Flowering habit.*—'Balriorose' is freely flowering under outdoor growing conditions with substantially continuous blooming from spring through autumn and year round in greenhouse environment.

*Time to first flower.*—Approximately 11 weeks after sticking of unrooted cutting.

*Lastingness of individual bloom.*—Approximately 1 day.

Flower description:

*Type.*—Solitary, rotate, not persistent. Quantity of fully open flowers per plant at eleven weeks: Approximately 7.

*Bud rate of opening.*—Generally takes 1 day for bud to progress from first color to fully open flower.

*Bud just before opening.*—Shape: Ovate. Length: Approximately 1.0 cm. Diameter: Approximately 7.2 mm. Texture: Glabrous. Color: Closest to 53A.

*Corolla.*—Form: Single. Diameter: Approximately 4.4 cm. Depth: Approximately 1.4 cm.

*Petals.*—Quantity: 5, overlapping. Shape: Obovate. Apex: Emarginate. Base: Truncate. Margin: Entire. Appearance: Shiny. Texture of upper and lower surfaces: Glabrous. Petal length: Approximately 2.2 cm. Petal width: Approximately 2.5 cm. Color of upper surface: N74A with "eye" at base of between 45A and 45B. Color of lower surface: N74A blending to N75D at base.

*Sepals.*—Quantity per flower: 2. Shape: Deltoid. Apex: Acuminate. Sepal length: Approximately 1.0 cm. Sepal width: Approximately 9.0 mm. Texture of upper and lower surfaces: Glabrous. Color of upper and lower surfaces: Translucent, 144C with venation of 144B.

*Reproductive organs.*—Androecium: Stamen quantity: Approximately 77. Stamen length: Approximately 3.0 mm. Filament color: 5B, translucent. Anther shape: Oblong, bilobed. Anther length: Approximately 0.5 mm. Anther color: Between 21A and N25A. Pollen amount: Abundant. Pollen color: 23A. Gynoecium: Pistil quantity: One per flower. Pistil length: Approximately 1.3 cm. Stigma shape: Five-branched. Stigma length: Approximately 4.5 mm. Stigma color: 61C with margins of 61B. Style length: Approximately 7.5 mm. Style color: 1B, translucent. Ovary diameter: Approximately 3.0 mm. Ovary color: 144A.

Seed and fruit production: Neither seed nor fruit production has been observed.

Disease and pest resistance: Resistance to pathogens and pests common to *Portulaca* has not been observed.

What is claimed is:

1. A new and distinct cultivar of *Portulaca* plant named 'Balriorose', substantially as herein shown and described.

* * * * *